United States Patent [19]
Caillat et al.

[11] Patent Number: 5,776,791
[45] Date of Patent: Jul. 7, 1998

[54] PROCESS FOR COLLECTIVE MANUFACTURE OF CHIPS WITH ELECTRODES SELECTIVELY COVERED BY A DEPOSIT

[75] Inventors: Patrice Caillat, Echirolles; Gérard Nicolas, Voreppe; Robert Teoule, Gernoble, all of France

[73] Assignee: Commissariat a l'Energie Atomique, Paris, France

[21] Appl. No.: 747,932

[22] Filed: Nov. 12, 1996

[30] Foreign Application Priority Data

Nov. 17, 1995 [FR] France ................... 95 13659

[51] Int. Cl.$^6$ ........................... H01L 21/66
[52] U.S. Cl. .......................... 438/15; 438/17
[58] Field of Search .................. 438/14, 15, 16, 438/17, 18

[56] References Cited

U.S. PATENT DOCUMENTS

| | | |
|---|---|---|
| 4,676,761 | 6/1987 | Poujois . |
| 5,008,617 | 4/1991 | Czubatys et al. ............ 438/17 |
| 5,103,557 | 4/1992 | Leedy . |
| 5,120,421 | 6/1992 | Glass et al. . |
| 5,256,578 | 10/1993 | Corley et al. ............... 438/17 |
| 5,389,556 | 2/1995 | Rostoker et al. ............ 438/15 |
| 5,422,498 | 6/1995 | Nikawa et al. .............. 438/17 |
| 5,472,561 | 12/1995 | Williams et al. ............ 438/17 |
| 5,543,334 | 8/1996 | Yoshii et al. ............... 438/17 |

OTHER PUBLICATIONS

Sensors and Actuators A, vol. A43, Nos. 1-3, pp.296-301, Jan. 1, 1994, R. Kakerow, et al., "A Monolithic Sensor Array Of Individually Addressable Microelectrodes".

Sensors and Actuators B, vol. B19, Nos. 1-3, pp. 675-677, 1994, G.C. Fiaccabrino, et al., "Array Of Individually Addressable Microelectrode".

Patent Abstracts of Japan, vol. 13, No. 460, Oct. 18, 1989, JP-A-01 179995, Jul. 18, 1989.

"Fluxless Flip-Chip Technology", Patrice Caillat, et al., pp. 1-5 no date.

Sensors and Actuators B, vol. B21, No. 1, pp. 33-37, T. Hermes, et al., "An Amperometric Microsensor Array With 1024 Individually Addressable Elements For Two-Dimensional Concentration Mapping" Sep. 1993.

*Primary Examiner*—Kevin Picardat
*Attorney, Agent, or Firm*—Oblon, Spivak, McClelland, Maier & Neustadt, P.C.

[57] ABSTRACT

This process comprises the following steps:

a) make a set of chips (110, 111, 112, 113) on a substrate (100), each chip including a number of electrodes (110a, 110b, 111a, 111b), b) individual validity test on each chip and the formation of at least one electrical network (117a, 117b) for addressable matched electrodes on different valid chips, c) make a deposit successively on matched electrode sets by dipping the substrate in an appropriate electrochemical bath and by application of appropriate voltages on the electrical network to cause an electrochemical reaction on the electrodes.

13 Claims, 5 Drawing Sheets

5,776,791

PROCESS FOR COLLECTIVE MANUFACTURE OF CHIPS WITH ELECTRODES SELECTIVELY COVERED BY A DEPOSIT

DESCRIPTION

1. Technical Field

This invention relates to a process for the collective manufacture of chips with electrodes selectively covered by a deposit.

The invention relates to applications particularly for the manufacture of sensors or other miniature sensitive elements in which chips with a large number of electrodes have to be made. These electrodes must be coated with appropriate materials, so that they can be adapted to their specific function in the sensor or the sensitive element.

For example, the invention is applicable to the manufacture of miniature elements such as "bio-chips" which are chips comprising part of an electric circuit made on a substrate such as an electrode field, and a biological part made on the surface of the chip. In this example, chemical compounds compatible with biological products should be deposited selectively on the electrodes.

2. Prior State of the Art

At the present time, known microelectronics processes such as lithography processes are used to form a deposit on the electrodes.

With this technique, a large number of chips can be treated simultaneously on a single semi-conductor slice, to selectively deposit a chemical compound on known electrodes on each chip.

As described in document (1), included in the references at the end of this description, a process for making deposits according to the first technique includes the following steps in sequence:

deposit of a continuous electrical conducting base layer on the semi-conductor slice, in contact with the electrodes on which a deposit is to be formed, formation of a resin layer on the continuous base layer, window openings in the resin above the chosen electrodes, electrochemical formation of the deposition material in the windows, using the continuous base layer as one electrode, with an independent counter electrode being placed in an electrochemical bath with the slice, elimination of the resin and the continuous base layer around the deposited material.

This process is conventional. It can make a local deposit of a metal or any other chemical compound on a substrate slice, for example on determined electrodes.

However, in some applications it is necessary to cover different electrodes of the same chip with different materials. These materials are used specifically for the special function of each electrode.

With the electrochemical process mentioned, if different materials are to be deposited on different sites or electrodes in a slice, it is necessary to form one resin layer for each different material to be deposited. When depositing each material, it is necessary to bare the regions in which the material must be deposited and to protect regions in which it must not be deposited.

The sequence of a large number of resin deposition and lithography operation steps to form the necessary openings corresponding to the electrodes to be coated with a given material, in each resin layer, makes the process complicated.

Furthermore, as illustrated in document (2) mentioned in the references at the end of this description, there is a known technique multiplexing electrodes on a chip to make an electrode matrix sensor from this chip, capable of making measurements of chemical or biochemical environments.

One purpose of this invention is to propose a collective chip treatment in order to make chips with the electrodes selectively covered by a deposit (the electrodes being multiplexed when there is a large number of electrodes per chip).

Another purpose of the invention is to propose a process that does not require a sequence of photolithography steps, or individual manipulation of each chip.

Another purpose of the invention is to propose a simple and reliable process that does not have the disadvantages or limitations mentioned above.

Another purpose of the invention is to propose a process capable of making a very large number of chips, each with a large number of electrodes, simultaneously and with a high manufacturing efficiency.

DESCRIPTION OF INVENTION

In order to achieve the purposes mentioned above, the objective of the invention is more precisely a collective manufacturing process for chips with electrodes selectively covered by a deposit, characterized in that the process includes the following steps:

a) make a set of chips on a substrate, each chip containing several electrodes, b) individual validity test on each chip and the formation of at least one network of electrical connections for addressing at least one set of "matched" electrodes, of different chips, each network being made according to a given connection plan and electrically connecting valid chips to each other, c) make a deposit on the electrodes in each set of matched electrodes in sequence, by dipping the support in an appropriate electrochemical bath and by applying appropriate polarization voltages on the connection network corresponding to the set of matched electrodes to selectively provoke an electrochemical reaction on the electrodes in the set of matched electrodes.

The substrate is dipped into another appropriate electrolytic bath whenever a different material is to be deposited on the electrodes.

For the purposes of this invention, a valid chip means a chip which has no defects preventing collective treatment of the set of chips.

Examples of preventive defects are short circuits in one of the chips which would connect its power supply to its ground. This type of defect could create a fault in all chips connected to it.

It is beneficial if the substrate (the slice) on which the chips are formed is cut when the deposits are made to isolate the chips so that they can be used separately.

While this cutting is being done, the electrical connections forming the network of chips are automatically cut.

The chips thus become electrically independent again and may be used individually in the application for which they are designed.

In this implementation, note that connecting chips together is only a temporary connection so that the deposit can be formed on some electrodes. This connection disappears when the substrate is cut, and each chip then recovers its own function. Thus, the connection network formed is simply an intermediate step and is not a final objective.

Note also that the connection network is not designed to create a common function to which each valid chip makes a contribution, but simply to make the selective deposit.

The order in which the steps in the chip individual validity tests are carried out and the chips are connected may be different depending on the embodiment of the invention.

In a first embodiment, step b) comprises the individual test on the validity of each chip in sequence, and then these valid chips are interconnected to each other.

In this embodiment of the invention, only valid chips are connected in the network so that a functional network can be formed directly.

In another embodiment, step b) includes the following steps in sequence:

the individual validity test on each chip, the connection of chips together in accordance with the connections plan, disconnection of invalid chips.

Invalid chips may be disconnected by sawing or by laser firing.

According to one aspect of the invention, the chips may be connected by electrical connections containing "fuse" points, that will melt under the effect of a laser beam to break the links. Disconnection is thus done by applying a laser beam on fuse points of electrical connections connecting invalid chips to the chip network.

The way in which the connection network(s) is (are) made may be different, depending on the number of electrodes in the chips.

A first possibility is to form a set of terminals, called the collective addressable terminals, on the substrate, and to connect a collective addressable terminal in each network of electrical connections, to the corresponding electrodes in a set of matched electrodes.

Thus a voltage applied to one of the collective terminals is transmitted to the various chips on each electrode in the corresponding set of matched electrodes.

Another possibility is to form terminals called individual addressable terminals on each chip, and to form a set of collective addressable terminals on the substrate. For example, individual addressable terminals for each chip can apply a selection address of one or several chip electrodes which must be raised to a potential appropriate to an electrochemical reaction, to a chip multiplexing circuit. This type of device is suitable for chips with a large number of electrodes. The multiplexing method is described in document (3) in the list of references at the end of this description. For information, for a chip with $2^n$ electrodes, for example $2_7=128$ electrodes, only n individual addressable terminals are necessary for a parallel type multiplexed structure. A single terminal is sufficient in a serial type multiplexed structure, although it is not as fast.

When forming the connection network, each individual addressable terminal is connected electrically to each valid chip, and to a corresponding collective terminal respectively, in accordance with a predetermined connection plan.

Regardless of whether the collective terminals are connected directly to the electrodes or to individual addressable terminals, the connection plan is drawn up preferably such that disconnecting an invalid chip in the connections network does not isolate a valid chip.

For example, individual terminals or electrodes may be connected in parallel and/or in series on the collective terminals.

The connections plan may also include redundant connections to guarantee connection of all valid chips, even if invalid chips are eliminated from the network.

According to one aspect of the invention, the formation of the connections network may comprise: a deposit of an electrical conducting material covered by a layer of photo-sensitive resin, over the entire substrate containing the chips, insolation of the resin in the fields corresponding to valid chips, the fields corresponding to adjacent valid chips containing marginal regions of mutual coverage in which there are patterns corresponding to conducting strips interconnecting chip connection lines; development of the resin and etching of the coat of conducting material in accordance with the patterns to form interconnecting strips.

The step in which deposits are formed on electrodes may be done in at least two different ways.

According to a first embodiment, the deposit is formed on the electrodes in each set of electrodes directly matched by the electrochemical reaction.

According to one alternative, for each set of matched electrodes, a layer of a chemical compound may be formed on all electrodes before provoking the electrochemical reaction, and the chemical compound may be eliminated by the electrochemical reaction on all electrodes except for the electrodes in the set of addressed matched electrodes.

According to one aspect of the invention, before making the deposits in step c), it is possible to form a coat of photosensitive material on at least some electrodes. When making the deposits in step c), the electrodes are then subjected to light radiation, for example ultraviolet, which activates the electrochemical reaction on addressed matched electrodes.

According to another aspect of the invention, the deposit formed on the electrodes may be a deposit of active molecules chosen from the group of biochemical or biological molecules. The deposit may also be metallic or a polymer.

Other characteristics and advantages of this invention will be better understood from the following description which refers to the non-restrictive figures in the attached drawings, which are given for illustration purposes.

DETAILED DESCRIPTION OF METHODS OF USING THE INVENTION

Figure 1:
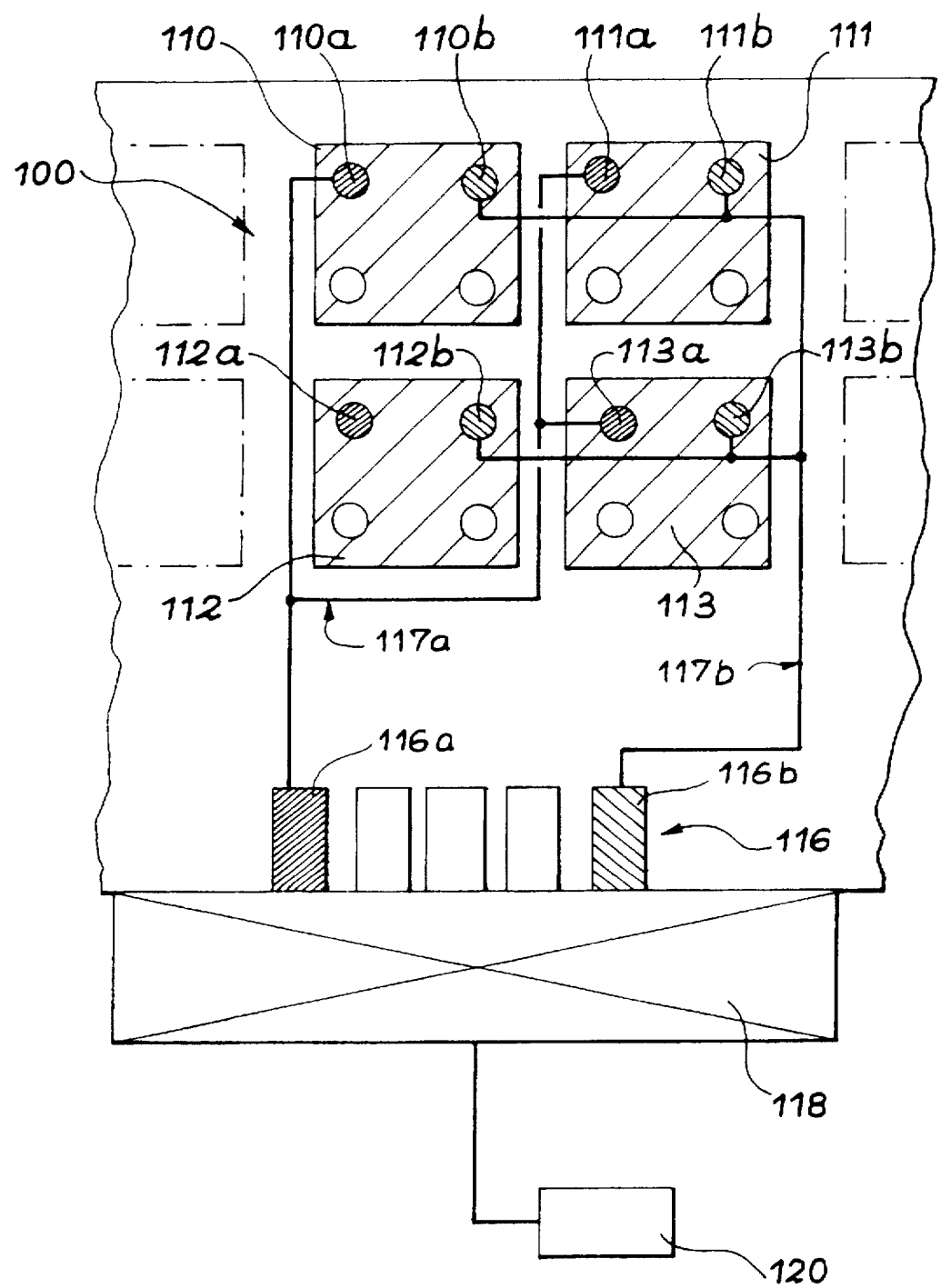
FIG. 1 shows an example of collective manufacture of chips connected in a connections network.

FIG. 1 shows a support substrate 100 on which several electronic chips 110, 111, 112, 113 are made. The chips are made using standard microelectronic processes.

For reasons of clarity, only four chips 110, 111, 112, 113 are shown in the figure, however the same substrate slice may include a large number of chips, for example 20 to 2,000.

In the example shown, chips 110, 111, 112, 113 are identical to each other. Each includes a limited number of electrodes. In order to distinguish between them, electrodes in chips each have the same reference as the chip followed by a letter a or b, respectively.

Substrate 100 also comprises addressable terminals 116, 116a, 116b connected to a connector 118. Terminals 116, 116a, 116b are preferably made at the periphery of the substrate 100. A voltage source 120 shown very diagrammatically is applied through connector 118 to terminals 116, with voltages appropriate for selectively initiating electrochemical deposits on some electrodes. Another terminal from the voltage source is connected to a counter electrode immersed in an appropriate electrochemical solution.

As shown in FIG. 1, sets of matched electrodes are defined on the substrate board. Matched electrodes are located on different chips, and are connected to an addressable terminal 116, also called the collective addressable terminal.

Thus for example, electrodes 110a, 111a, 112a, 113a, forming a first set of matched electrodes, are connected to terminal 116a. Electrodes 110b, 111b, 112b, 113b form a second set of matched electrodes. Connections networks, i.e. electrical connections that connect electrodes in the first and second sets of matched electrodes to terminals 116a and 116b respectively, are marked with references 117a and 117b respectively.

Electrical connections not shown connect other matched electrodes to each other and to addressable terminals, in the same way. Therefore, chips are electrically connected in the connections networks.

In the example shown in the figure, the electrical connections are directly connected to the electrodes. An individual test on the chips makes a distinction between valid chips and invalid chips. The electrodes in invalid chips are not connected to terminals 116.

The entire slice 100 equipped with chips 110, 111, 112 and 113 is dipped in an electrochemical bath corresponding to a chemical compound to be deposited on the electrodes of one of the sets of matched electrodes.

An appropriate voltage output by the voltage source is applied through connector 118 to a collective terminal, for example 116a, which corresponds to the chosen set of matched electrodes 110a, 111a, 112a, 113a.

The voltage transmitted to the electrodes concerned through the interconnections network 117a provokes a deposit of the chemical compound for these electrodes.

The substrate slice may then be rinsed, and then dipped sequentially in as many electrochemical baths as are necessary to deposit different chemical compounds on the electrodes of different sets of matched electrodes, by applying appropriate voltages on terminals 116.

Figure 2:
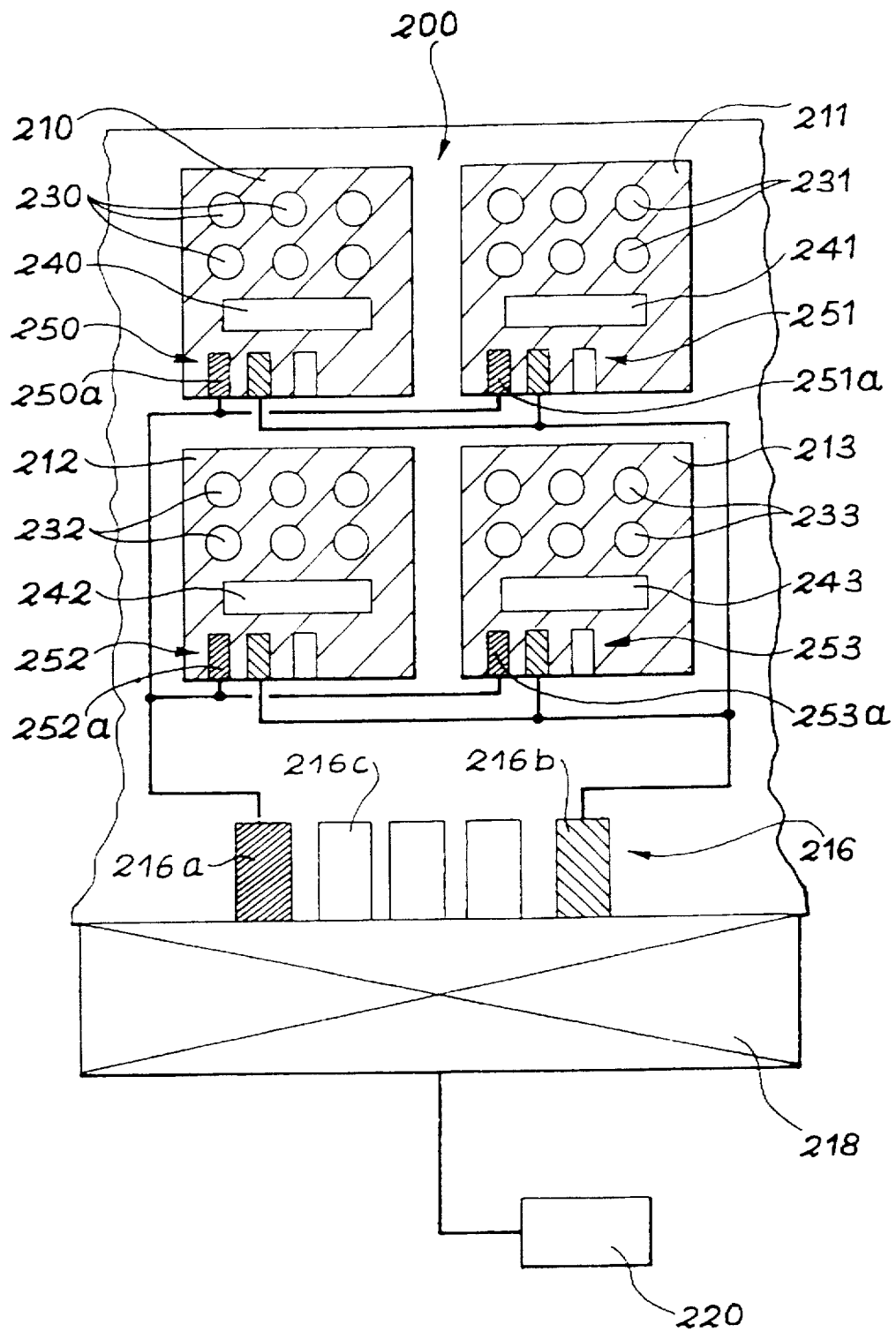
FIG. 2 shows another example of collective manufacture of chips connected in a connections network.

FIG. 2 shows another example of how to make a substrate slice equipped with several chips. This example is applicable particularly to chips that contain a large number of electrodes.

The references are identical to those assigned to identical or similar elements in FIG. 1, plus 100.

Thus FIG. 2 shows a substrate 200 on which several chips 210, 211, 212, 213 are formed. Only a few chips are shown, in order to make the figure easier to read.

Each chip comprises a large number of electrodes 230, 231, 232 and 233, a multiplexing circuit 240, 241, 242, 243 and a set of individual addressable terminals 250, 251, 252, 253.

Substrate 200 also comprises collective addressable terminals 216. A connector 218 connects terminals 216 to an outside voltage source 220 capable of outputting addressing signals. For example, the outside voltage source could be a specially adapted microcomputer interface.

After carrying out a validity test on the chips, the chips are connected to each other in chip networks. The networks are formed in accordance with connection plans in which equivalent individual addressable terminals on each chip are connected to the corresponding collective addressable terminals on the substrate.

For example, the individual terminals 250a, 251a, 252a and 253a on chips 210, 211, 212, 213 are all connected to each other and to a corresponding collective terminal 216a.

The internal multiplexing circuit 240, 241, 242, 243 on each chip selectively addresses one or several selected electrodes, as a function of an addressing signal which for example may be applied to one of the chip individual terminals.

For example, electrode addressing signals originating from collective terminal 216a are applied to a first addressable terminal 250a, 251a, 252a, 253a on each chip.

Second individual terminals on each chip, for example connected to collective terminal 216b, are provided for the chip electrical power supply.

Third individual terminals on each chip are connected for example to the collective terminal 216a through links not shown in FIG. 2. These terminals are designed to supply a working voltage to each chip, i.e. a voltage appropriate to the intended chemical reaction, this voltage being distributed on the electrode(s) addressed by the internal multiplexing circuit in each chip.

Finally, fourth individual terminals on chips (not shown) may be connected to a collective substrate terminal to reset chips to logical zero.

Figure 3:
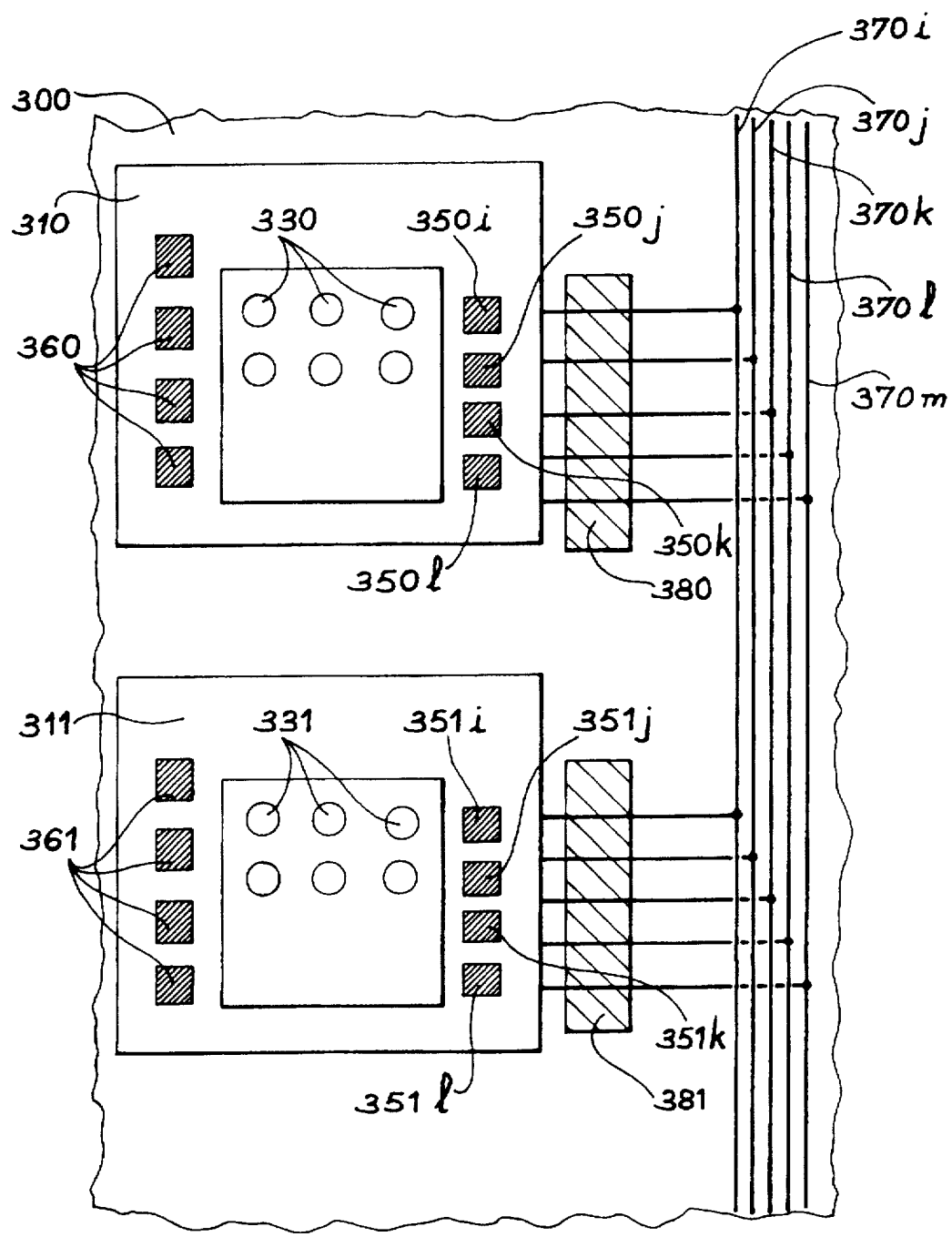
FIG. 3 is a view of chips at an enlarged scale and shows an example of chip interconnections.

FIG. 3 shows a chip interconnection example on a larger scale. Each of two approximately identical chips 310, 311 includes a set of electrodes 330, 331 and a set of individual addressable terminals referenced 350i, 350j, 350k, 350l, 351i, 351j, 351k and 351l.

Each chip also comprises a set of individual test pins 360, 361. These pins are provided to cooperate with a conventional test card with pins.

Electrical connection lines 370i, 370j, 370k, 370l are provided close to the chips on substrate 300, and are connected to chip 310 individual terminals 350i, 350j, 350k, 350l respectively, and to chip 311 individual terminals 351i, 351j, 351k, 351l. Chip individual terminals are preferably connected to these connection lines in parallel so that invalid chips can be isolated without affecting the operation of surrounding valid chips.

The substrate also comprises "reconfiguration" zones 380, 381 associated with each chip respectively. The electrical connection lines in these zones, connecting connection terminals to lines 370i, 370j, 370k, 370l may be melted.

According to one embodiment of the invention, all chips are initially interconnected in accordance with the previously described interconnection plan. The chips are then tested by applying and measuring test voltages on pins 360, 361. This test distinguishes valid chips from chips which have a defect such as a short circuit.

Invalid chips are isolated from the connection network by laser firing in the corresponding reconfiguration zone, to melt the fuse points on connection lines in this zone, and cut these lines.

Figure 4A:
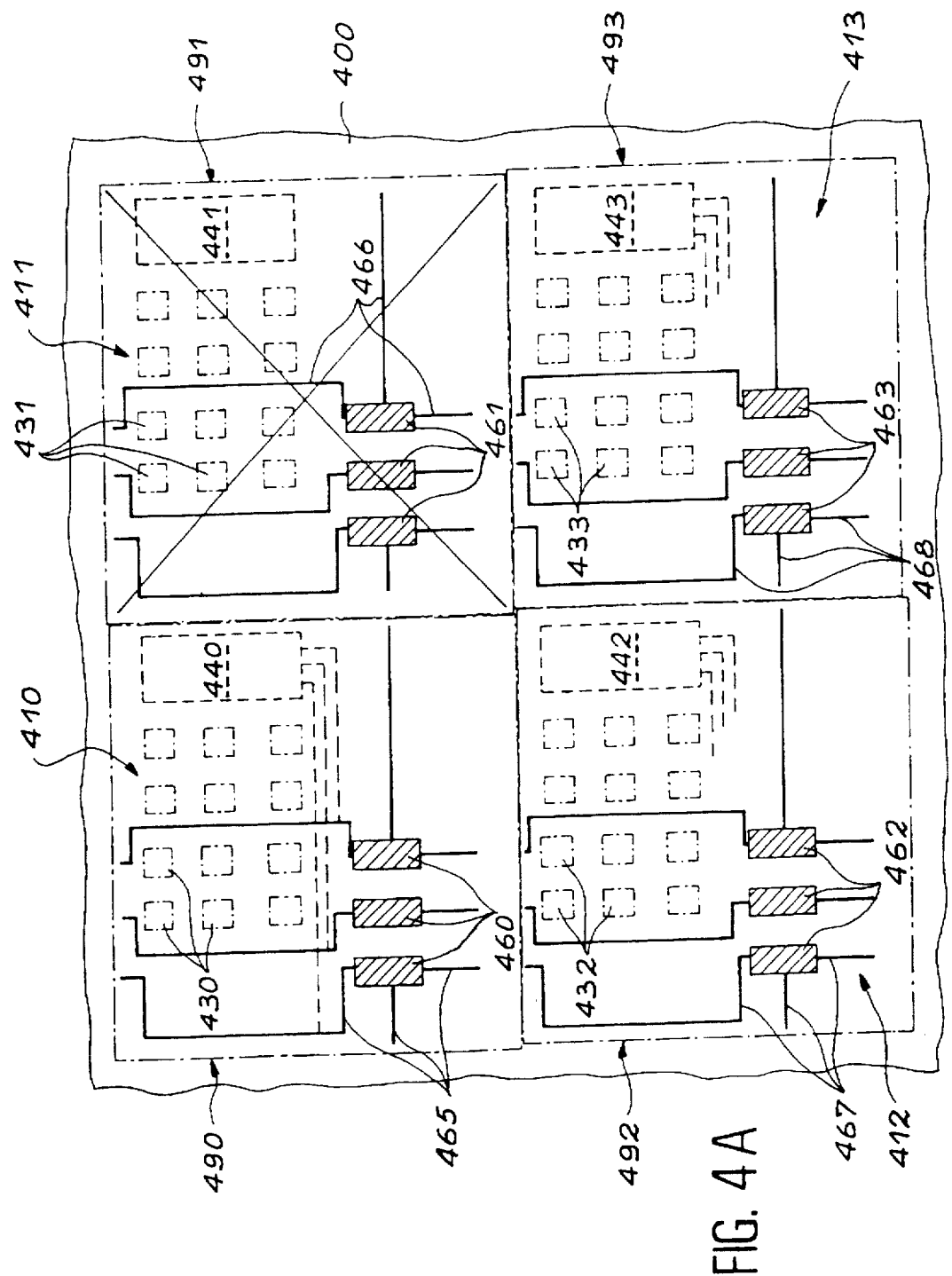
FIGS. 4A and 4B show the photolithography fields corresponding to each successive step in the collective manufacture of chips according to the invention.
Figure 4B:
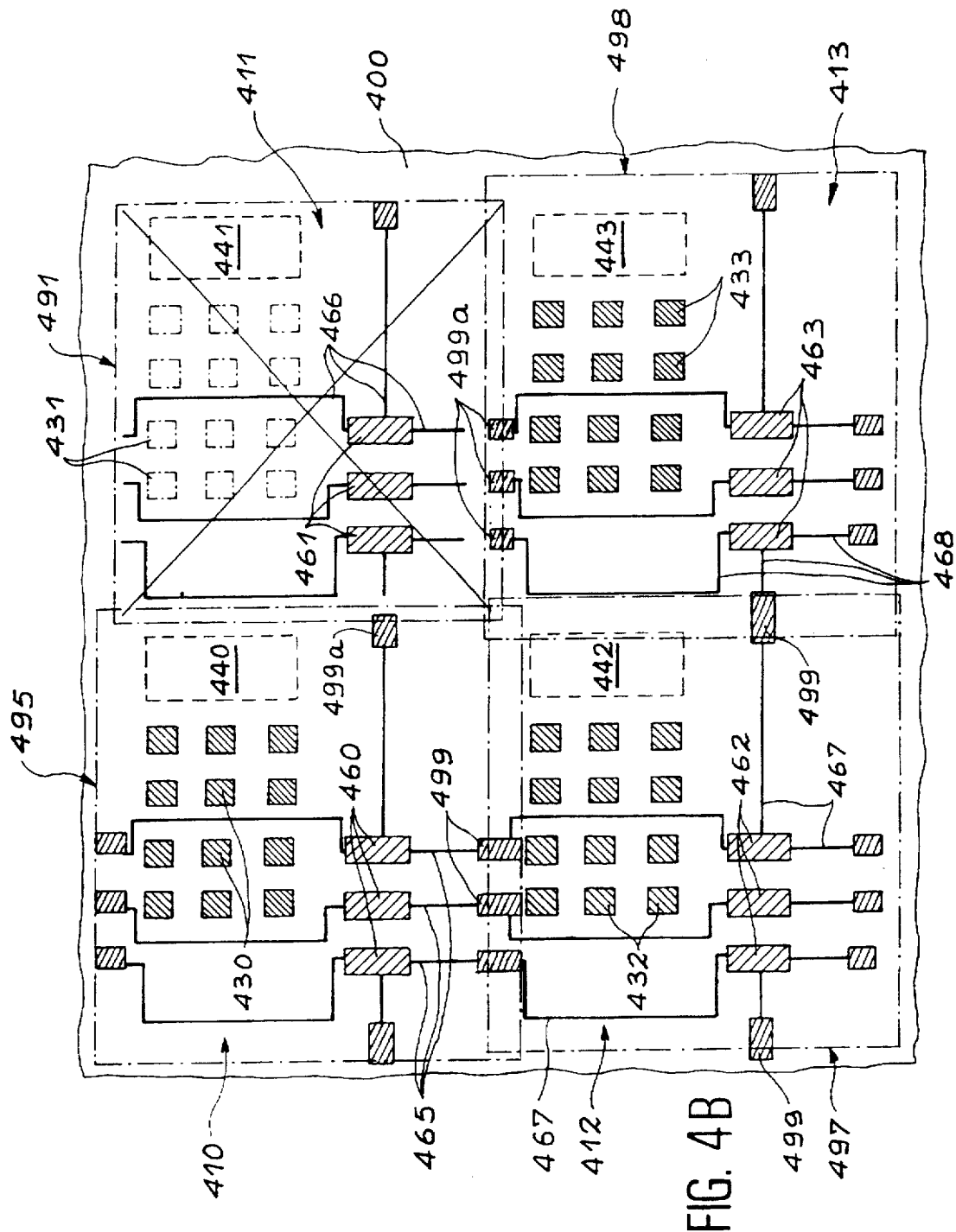

FIGS. 4A and 4B illustrate how chips are made collectively on a substrate.

FIG. 4A shows a photolithography step and shows a portion of a substrate 400 in which practically identical chips 410, 411, 412, 413 are made, at a larger scale.

The chips include different elements such as for example a multiplexing circuit 440, 441, 442, 443, electrodes 430, 431, 542, 433 and test pins 460, 461, 462, 463.

The various elements are made during different lithography steps corresponding to various superimposed conducting levels. During these lithography steps, a layer of conducting material and a layer of resin are deposited on the substrate slice. The resin is insolated through a mask corresponding to patterns to be made in the conducting layer. After the resin has developed, the conducting material layer is etched to eliminate parts not protected by the resin.

Not the entire resin layer is insolated simultaneously, due to the relatively large size of the substrate.

Portions of the resin layer are insolated in sequence, through the same mask which is moved relative to the substrate in an apparatus usually referred to as a "stepper" or "photorepeater".

These portions are referred to by the term "field" and for example may correspond to the location of a chip on the substrate.

Four fields 490, 491, 492, 493, corresponding to chips 410, 411, 412, 413 respectively, are shown in FIG. 4A.

Note that the fields are adjacent. In the fields in FIG. 4A, conducting patterns are made corresponding to test pins 460, 461, 462, 463 and to connection lines 465, 466, 467, 468 extending from these pins to marginal regions of fields.

FIG. 4A shows a last but one conducting level.

In this conducting level, the ends of the connection lines are not connected together and the chips are electrically isolated.

Note that multiplexing circuits 440, 441, 442, 443 which are made before the lithography step in the FIG. 4, and the locations of electrodes 410, 411, 412 and 413 which are made after the lithography step, are shown in discontinuous lines.

When the test pins have been completed, each chip is tested individually in order to check if it is valid.

FIG. 4B shows the final lithography step for forming the last conducting level.

This step is carried out in the second fields 495, 497 and 498 corresponding to chips 410, 412, 413 that the individual test has determined are valid.

The second insolation fields 495, 497 and 498 are larger than the corresponding first fields 490, 492, 493 on which they are approximately superimposed. Fields 495 and 497 have marginal overlapping regions, and fields 497 and 498 also have marginal overlapping regions. In these regions, patterns 499 are provided corresponding to interconnecting conducting strips to connect connection lines facing 465 and 467, and 467 and 468 together.

The part of the substrate corresponding to field 491 is not insolated during the last lithography step. Therefore, the conducting material in the last conducting level is completely eliminated from this layer and chip 411, considered to be invalid during the individual test, remains isolated.

Parts of pattern 499a are formed around the periphery of fields 495 and 498 facing towards field 491. However, there is no corresponding part of the pattern on field 491, nor sufficient overlap to interconnect line 466 on chip 411 with the lines 465 and 468 facing chips 410 and 413.

Electrical isolation of chip 411 does not eliminate the connection of adjacent chips in the connections network, due to redundancy in the connection lines.

The end result is one or several networks to which only valid chips are connected.

Each network is connected to one of several collective addressable terminals formed on the substrate to apply suitable voltages to chips in order to initiate electrochemical reactions. These terminals are not shown on FIGS. 4A and 4B.

LIST OF DOCUMENTS MENTIONED IN THIS APPLICATION (1) "Fluxless Flip-Chip Technology" by P. Caillat and G. Nicolas.

(2) "A monolithic sensor array of individually addressable microelectrodes" by R. Kakerow et al. in "Sensors and Actuators" A, 43 (1994) pp. 296–301.

(3) "Array of individually addressable microelectrodes" by G. C Fiaccabrino et al., in "Sensors and Actuators" B, 18–19 (1994), pp. 675–677.

We claim:

1. Process for collective manufacture of chips comprising electrodes selectively covered by a deposit, characterized in that the process comprises the following steps:

a) make a set of chips (110, 210, 310, 410, 111, 211, 311, 411, 112, 212, 412, 113, 213, 413) on a substrate (100, 200, 300, 400), each comprising several electrodes (110a, 110b, 111a, 111b, 230, 231, 232, 233, 330, 331, 430, 431, 432, 433), b) individual validity test on each chip, and the formation of at least one network of electrical connections (117a, 117b, 370i, 370j, 370k, 370l, 465, 466, 467, 468, 499) for addressing at least one set of "matched" electrodes of different chips, each network being made in accordance with a given connections plan and electrically connecting valid chips to each other, c) make a deposit on electrodes in each set of matched electrodes in sequence, by dipping the substrate in an appropriate electrochemical bath and by applying appropriate polarization voltages on the connections network corresponding to the set of matched electrodes, to selectively provoke an electrochemical reaction on the electrodes in the set of matched electrodes.

2. Process according to claim 1, characterized in that step b) comprises the individual test on the validity of each chip, then the connection of valid chips to each other, in sequence.

3. Process according to claim 1, characterized in that step b) comprises the following in sequence:

individual validity test on each chip, connection of chips to each other in accordance with the connection plan, disconnection of invalid chips.

4. Process according to claim 3, characterized in that chips are connected by electrical connections including "fuse" points (380), which can be melted under the effect of a laser beam to cut the links, the disconnection being done by applying a laser beam to fuse points of electrical connections connecting invalid chips to the chips network.

5. Process according to claim 1, characterized in that a set of terminals (116, 216) called collective addressable terminals are formed on the substrate (100, 200), and a collective addressable terminal is connected to a set of matched electrodes in each network of electrical connections.

6. Process according to claim 1, characterized in that terminals called individual addressable terminals (250, 251, 252, 253) for chip electrodes are made on each chip, and a set of terminals called collective addressable terminals (216, 216a, 216b) are made on the substrate, and when the connection network is being formed, each individual addressable terminal for each valid chip is electrically connected to the corresponding collective terminal, in accordance with the connection plan.

7. Process according to claim 1, characterized in that a layer of photosensitive material is formed before step c) on at least some electrodes, and that a light radiation is applied to the electrodes in step c), to activate the electrochemical reaction.

8. Process according to claim 1, characterized in that the deposit is formed directly on the electrodes in each set of matched electrodes by the electrochemical reaction.

9. Process according to claim 1, characterized in that before provoking the electrochemical reaction for each set of matched electrodes, a layer of a chemical compound is formed on all electrodes, and the chemical compound is eliminated by the electrochemical reaction on all electrodes except for the electrodes in the set of matched addressed electrodes.

10. Process according to claim 1, characterized in that after making deposits on each set of electrodes, the support is cut out to separate chips from each other.

11. Process according to claim 1, characterized in that the chips are approximately identical and each set of matched electrodes comprises an electrode of each chip.

12. Process according to claim 1, characterized in that the deposit made on the electrodes is a set of active molecules chosen from the group of biochemical or biological molecules.

13. Process according to claim 1, characterized in that formation of the connections network includes:

deposit of a layer of electrical conducting material covered by a layer of photosensitive resin, over the entire substrate containing the chips, insolation of the resin in fields (495, 497, 498) corresponding to valid chips, and fields corresponding to adjacent valid chips with marginal regions of mutual coverage in which patterns (499) are provided corresponding to chip connection lines interconnecting conducting strips, development of the resin and etching the layer of conducting material according to the patterns to form interconnecting strips.

* * * * *